(12) United States Patent
Chakravarti et al.

(10) Patent No.: US 9,365,466 B2
(45) Date of Patent: Jun. 14, 2016

(54) METHOD AND SYSTEM FOR PRODUCING A LIQUID HYDROCARBON PRODUCT FROM A FISCHER-TROPSCH PROCESS USING A SYNTHESIS GAS PRODUCED FROM AN OXYGEN TRANSPORT MEMBRANE BASED REFORMING REACTOR

(71) Applicants: Shrikar Chakravarti, East Amherst, NY (US); Kenneth L. Burgers, East Amherst, NY (US); Raymond F. Drnevich, Clarence Center, NY (US); Ines C. Stuckert, Grand Island, NY (US)

(72) Inventors: Shrikar Chakravarti, East Amherst, NY (US); Kenneth L. Burgers, East Amherst, NY (US); Raymond F. Drnevich, Clarence Center, NY (US); Ines C. Stuckert, Grand Island, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 14/638,344

(22) Filed: Mar. 4, 2015

(65) Prior Publication Data
US 2015/0251967 A1    Sep. 10, 2015

Related U.S. Application Data

(60) Provisional application No. 61/948,249, filed on Mar. 5, 2014.

(51) Int. Cl.
| C07C 27/00 | (2006.01) |
| C07C 1/04 | (2006.01) |
| C01B 3/38 | (2006.01) |
| C01B 13/02 | (2006.01) |

(52) U.S. Cl.
CPC . *C07C 1/04* (2013.01); *C01B 3/382* (2013.01); *C01B 3/384* (2013.01); *C01B 13/0251* (2013.01); *C01B 2203/025* (2013.01); *C01B 2203/0233* (2013.01); *C01B 2203/0244* (2013.01); *C01B 2203/0255* (2013.01); *C01B 2203/062* (2013.01); *C01B 2203/0811* (2013.01); *C01B 2203/0838* (2013.01); *C01B 2203/0844* (2013.01); *C01B 2203/1241* (2013.01); *C01B 2203/142* (2013.01)

(58) Field of Classification Search
CPC .............. C01B 2203/0838; C01B 2203/0811; C01B 3/384; C01B 3/382; C01B 2203/025; C01B 2203/0244; C01B 2203/142; C01B 2203/0844; C01B 2203/0255; C01B 13/0251; C01B 2203/062; C10G 2/30; C10G 2/32; C07C 1/04
USPC .................................................. 518/700, 702
See application file for complete search history.

(56) References Cited

U.S. PATENT DOCUMENTS

| 5,980,840 | A | 11/1999 | Kleefisch et al. |
| 6,048,472 | A | 4/2000 | Nataraj et al. |
| 6,110,979 | A | 8/2000 | Nataraj et al. |
| 6,114,400 | A | 9/2000 | Nataraj et al. |
| 6,296,686 | B1 | 10/2001 | Prasad et al. |
| 7,261,751 | B2 | 8/2007 | Dutta et al. |
| 8,349,214 | B1 | 1/2013 | Kelly et al. |

FOREIGN PATENT DOCUMENTS

WO    WO 2013/009560 A1    1/2013

*Primary Examiner* — Jafar Parsa
(74) *Attorney, Agent, or Firm* — Ralph J. Mancini

(57) ABSTRACT

A system and method for producing a liquid hydrocarbon product from a Fischer-Tropsch process using a synthesis gas feed produced in an oxygen transport membrane based reforming reactor. The system and method involve reforming a mixed feed stream comprising natural gas, hydrogen and the Fischer-Tropsch tail gas, in a reforming reactor in the presence of steam, radiant heat from oxygen transport membrane elements and a reforming catalyst to produce a reformed synthesis gas stream comprising hydrogen, carbon monoxide, and unreformed hydrocarbon gas. The reformed synthesis gas stream is further reformed in an oxygen transport membrane based reforming reactor and conditioned to produce a synthesis gas product stream preferably having a H2/CO ratio of from about 1.7 to about 2.2. The synthesis gas product stream is then synthesized using a Fischer Tropsch process to produce the liquid hydrocarbon product and a Fischer-Tropsch tail gas.

22 Claims, 6 Drawing Sheets

| FT Tail Gas to Syngas Process | 0% | 20% | 40% | 60% | 70% | 71% | 72% | 74% | 76% | 78% | 80% |
|---|---|---|---|---|---|---|---|---|---|---|---|
| Natural Gas/Product, scf/bbl* | 15,330 | 14,057 | 12,699 | 11,205 | 10,340 | 10,247 | 10,243 | 10,227 | 10,198 | 10,172 | 10,172 |
| NG to Process, MMSCFD | 6.13 | 5.62 | 5.08 | 4.48 | 4.14 | 4.10 | 4.06 | 3.98 | 3.93 | 3.87 | 3.84 |
| NG to Fuel, MMSCFD | 0.00 | 0.00 | 0.00 | 0.00 | 0.00 | 0.00 | 0.03 | 0.11 | 0.15 | 0.20 | 0.23 |
| Total NG, MMSCFD | 6.13 | 5.62 | 5.08 | 4.48 | 4.14 | 4.10 | 4.10 | 4.09 | 4.08 | 4.07 | 4.07 |
| Air Rate, MMSCFD | 24.73 | 23.57 | 22.30 | 20.79 | 19.90 | 19.79 | 19.69 | 19.47 | 19.30 | 19.13 | 19.06 |
| O2 to OTM, tpd | 137.80 | 131.30 | 124.20 | 115.80 | 10.90 | 10.30 | 109.70 | 18.50 | 107.50 | 106.60 | 16.20 |
| Steam to Process Rate, kpph | 18.12 | 17.43 | 16.60 | 15.32 | 14.57 | 14.53 | 14.49 | 14.32 | 14.17 | 14.04 | 14.11 |
| FT Tail Gas to Process Feed, MMSCFD | 0.00 | 0.67 | 1.40 | 2.23 | 2.72 | 2.78 | 2.83 | 2.95 | 2.87 | 2.75 | 2.82 |
| FT Tail Gas to Fuel, MMSCFD | 0.00 | 0.00 | 0.00 | 0.28 | 1.04 | 1.13 | 1.10 | 1.04 | 0.91 | 0.77 | 0.71 |
| FT Tail Gas to Flare, MMSCFD | 3.28 | 2.70 | 2.10 | 1.20 | 0.12 | 0.00 | 0.00 | 0.00 | 0.00 | 0.00 | 0.00 |
| Total FT Tail Gas, MMSCFD | 3.28 | 3.37 | 3.50 | 3.71 | 3.89 | 3.91 | 3.93 | 3.98 | 3.78 | 3.52 | 3.53 |
| Syngas to H2 Membrane | 40.61% | 34.40% | 26.20% | 14.20% | 5.10% | 3.99% | 2.90% | 0.40% | 0.00% | 0.00% | 0.00% |
| H2 to Fuel/Feed, MMSCFD | 1.68 | 1.62 | 1.57 | 1.20 | 0.41 | 0.32 | 0.23 | 0.03 | 0.00 | 0.00 | 0.00 |
| H2 to Flare, MMSCFD | 2.53 | 1.75 | 0.84 | 0.00 | 0.00 | 0.00 | 0.00 | 0.03 | 0.00 | 0.00 | 0.00 |
| Total H2, MMSCFD | 4.20 | 3.37 | 2.40 | 1.20 | 0.41 | 0.32 | 0.23 | 0.03 | 0.00 | 0.00 | 0.00 |
| Syngas H2:CO Ratio (pre membrane) | 2.97 | 2.80 | 2.60 | 2.36 | 2.20 | 2.19 | 2.17 | 2.13 | 2.07 | 1.98 | 1.90 |
| Stream 315 H2:CO Ratio (Syngas to FT) | 2.13 | 2.13 | 2.13 | 2.13 | 2.13 | 2.13 | 2.13 | 2.13 | 2.07 | 1.98 | 1.90 |
| Power Generated, kW | 466 | 460 | 453 | 448 | 447 | 447 | 446 | 445 | 438 | 430 | 426 |
| Power Required, kW | 466 | 460 | 453 | 448 | 447 | 447 | 446 | 445 | 438 | 430 | 426 |

Steam to carbon ratio: 1.5; OTM outlet pressure: 460 psia; OTM outlet temperature: 1800F; FT product rate: 400 BBL/d

FIG. 3

| FT Tail Gas to Syngas Process | 0% | 20% | 40% | 60% | 70% | 71% | 72% | 74% | 76% | 78% | 80% |
|---|---|---|---|---|---|---|---|---|---|---|---|
| Stream 315 (Syngas to FT) Composition (%) | | | | | | | | | | | |
| Hydrogen | 59.618 | 59.266 | 58.773 | 57.962 | 57.316 | 57.231 | 57.153 | 56.964 | 55.991 | 54.721 | 53.337 |
| Nitrogen | 0.363 | 0.412 | 0.490 | 0.636 | 0.775 | 0.794 | 0.814 | 0.858 | 0.929 | 1.017 | 1.109 |
| Water | 0.278 | 0.292 | 0.309 | 0.333 | 0.350 | 0.352 | 0.354 | 0.358 | 0.360 | 0.361 | 0.363 |
| Carbon monoxide | 28.029 | 27.864 | 27.632 | 27.251 | 26.947 | 26.907 | 26.870 | 26.781 | 27.120 | 27.578 | 28.038 |
| Carbon dioxide | 10.008 | 10.641 | 11.481 | 12.736 | 13.682 | 13.801 | 13.912 | 14.174 | 14.785 | 15.567 | 16.452 |
| Methane | 1.701 | 1.523 | 1.313 | 1.080 | 0.929 | 0.913 | 0.895 | 0.863 | 0.811 | 0.755 | 0.700 |
| Ammonia | 0.002 | 0.002 | 0.002 | 0.002 | 0.002 | 0.002 | 0.002 | 0.002 | 0.002 | 0.002 | 0.002 |

Steam to carbon ratio: 1.5; OTM outlet pressure: 460 psia; OTM outlet temperature: 1800F; FT product rate: 400 BBL/d

FIG. 4

| FT Tail Gas to Syngas Process | 0% | 30% | 60% | 70% | 75% | 77% | 78% | 79% | 80% |
|---|---|---|---|---|---|---|---|---|---|
| Natural Gas/Product, scf/bbl | 16,578 | 14,471 | 12,044 | 11,062 | 10,662 | 10,636 | 10,623 | 10,609 | 10,595 |
| NG to Process, MMSCFD | 6.63 | 5.79 | 4.82 | 4.43 | 4.20 | 4.09 | 4.04 | 4.00 | 3.97 |
| NG to Fuel, MMSCFD | 0.00 | 0.00 | 0.00 | 0.00 | 0.07 | 0.16 | 0.21 | 0.25 | 0.27 |
| Total NG, MMSCFD | 6.63 | 5.79 | 4.82 | 4.43 | 4.26 | 4.25 | 4.25 | 4.24 | 4.24 |
| Air Rate, MMSCFD | 27.81 | 25.66 | 23.01 | 21.89 | 21.21 | 20.90 | 20.74 | 20.61 | 20.52 |
| O2 to OTM, tpd | 155.00 | 142.90 | 128.20 | 122.00 | 118.20 | 116.40 | 115.50 | 114.80 | 114.30 |
| Steam to Process Rate, kpph | 26.19 | 24.23 | 21.65 | 20.45 | 19.72 | 19.55 | 19.33 | 19.33 | 19.09 |
| FT Tail Gas to Process Feed, MMSCFD | 0.00 | 1.14 | 2.50 | 3.08 | 3.43 | 3.60 | 3.68 | 3.70 | 3.63 |
| FT Tail Gas to Fuel, MMSCFD | 0.00 | 0.00 | 0.00 | 0.73 | 1.15 | 1.07 | 1.04 | 0.98 | 0.91 |
| FT Tail Gas to Flare, MMSCFD | 3.59 | 2.65 | 1.67 | 0.59 | 0.00 | 0.00 | 0.00 | 0.00 | 0.00 |
| Total FT Tail Gas, MMSCFD | 3.59 | 3.78 | 4.17 | 4.41 | 4.58 | 4.67 | 4.72 | 4.68 | 4.53 |
| Syngas to H2 Membrane | 50.12% | 40.06% | 23.06% | 13.33% | 6.44% | 3.03% | 1.12% | 0.00% | 0.00% |
| H2 to Fuel/Feed, MMSCFD | 2.08 | 1.98 | 1.85 | 1.16 | 0.54 | 0.25 | 0.09 | 0.00 | 0.00 |
| H2 to Flare, MMSCFD | 3.76 | 2.28 | 0.29 | 0.00 | 0.00 | 0.00 | 0.00 | 0.00 | 0.00 |
| Total H2, MMSCFD | 5.84 | 4.25 | 2.14 | 1.16 | 0.54 | 0.25 | 0.09 | 0.00 | 0.00 |
| Syngas H2:CO Ratio (pre membrane) | 3.29 | 2.95 | 2.53 | 2.34 | 2.23 | 2.17 | 2.14 | 2.10 | 2.05 |
| Stream 315 H2:CO Ratio (Syngas to FT) | 2.13 | 2.13 | 2.13 | 2.13 | 2.13 | 2.13 | 2.13 | 2.10 | 2.05 |
| Power Generated, kW | 513 | 501 | 492 | 490 | 488 | 488 | 487 | 485 | 480 |
| Power Required, kW | 513 | 501 | 492 | 490 | 488 | 488 | 487 | 485 | 480 |

Steam to carbon ratio: 2.0; OTM outlet pressure: 460 psia; OTM outlet temperature: 1800F; FT product rate: 400 BBL/d

FIG. 5

| FT Tail Gas to Syngas Process | 0% | 30% | 60% | 70% | 75% | 77% | 78% | 79% | 80% |
|---|---|---|---|---|---|---|---|---|---|
| Stream 315 (Syngas to FT) Composition (%) | | | | | | | | | |
| Hydrogen | 58.474 | 57.723 | 56.342 | 55.512 | 54.923 | 54.623 | 54.455 | 53.988 | 53.133 |
| Nitrogen | 0.383 | 0.467 | 0.658 | 0.794 | 0.896 | 0.948 | 0.977 | 1.016 | 1.070 |
| Water | 0.258 | 0.282 | 0.319 | 0.338 | 0.351 | 0.358 | 0.361 | 0.364 | 0.365 |
| Carbon monoxide | 27.491 | 27.138 | 26.489 | 26.099 | 25.822 | 25.681 | 25.602 | 25.660 | 25.894 |
| Carbon dioxide | 12.299 | 13.483 | 15.516 | 16.682 | 17.494 | 17.904 | 18.133 | 18.517 | 19.107 |
| Methane | 1.093 | 0.905 | 0.674 | 0.574 | 0.511 | 0.485 | 0.471 | 0.453 | 0.430 |
| Ammonia | 0.002 | 0.002 | 0.002 | 0.002 | 0.002 | 0.002 | 0.002 | 0.002 | 0.002 |

Steam to carbon ratio: 2.0; OTM outlet pressure: 460 psia; OTM outlet temperature: 1800F; FT product rate: 400 BBL/d

FIG. 6

METHOD AND SYSTEM FOR PRODUCING A LIQUID HYDROCARBON PRODUCT FROM A FISCHER-TROPSCH PROCESS USING A SYNTHESIS GAS PRODUCED FROM AN OXYGEN TRANSPORT MEMBRANE BASED REFORMING REACTOR

CROSS REFERENCE TO RELATED APPLICATIONS

The present application claims the benefit of and priority to U.S. provisional patent application Ser. No. 61/948,249 filed on Mar. 5, 2014, the disclosure of which is incorporated by reference herein.

FIELD OF THE INVENTION

The present invention relates to the production of liquid hydrocarbon products in a Fischer-Tropsch process, and more particularly to a method and system for producing liquid hydrocarbon products using synthesis gas produced from an oxygen transport membrane based reforming reactor.

BACKGROUND

The catalytic hydrogenation of carbon monoxide to produce light gases, liquids and waxes, ranging from methane to heavy hydrocarbons ($C_{80}$ and higher) in addition to oxygenated hydrocarbons, is typically referred to as Fischer-Tropsch or FT synthesis. Traditional FT processes primarily produce a high weight percent FT wax ($C_{25}$ and higher) from the catalytic conversion process. These FT waxes are then hydrocracked and/or further processed to produce diesel, naphtha, and other fractions. During this hydro-cracking process, light hydrocarbons are also produced, which may require additional upgrading to produce viable products. These processes are well known and described in the art.

As indicated above, the costs associated with the production of synthesis gas for use in an FT process, such as liquid fuel production, represent a significant portion of the total cost of the plant and the quality characteristics of the synthesis gas is critical to the efficient operation of the plant. The synthesis gas used in the FT synthesis is typically characterized by the hydrogen to carbon monoxide ratio (H2:CO). A H2:CO ratio of from about 1.8 to about 2.1 defines the desired ratio of synthesis gas used in many gas to liquids production process.

Synthesis gas containing hydrogen and carbon monoxide is produced for a variety of industrial applications. Conventionally, the synthesis gas is produced in a steam methane reforming (SMR) process using a fired reformer in which natural gas and steam are reformed in nickel catalyst containing reformer tubes at high temperatures (e.g., 850° C. to 1000° C.) and moderate pressures (e.g., 16 to 30 bar). The endothermic heating requirements for steam methane reforming reactions occurring within the reformer tubes are provided by burners firing into the furnace that are fueled by part of the natural gas. In order to increase the hydrogen content of the synthesis gas produced by the steam methane reforming (SMR) process, the synthesis gas can be subjected to water-gas shift reactions to react residual steam in the synthesis gas with the carbon monoxide.

A well-established alternative to steam methane reforming is the non-catalytic partial oxidation process (POx) whereby a sub-stoichiometric amount of oxygen is allowed to react with the natural gas feed creating steam and carbon dioxide at high temperatures. The high temperature residual methane is reformed through catalytic reactions with the high temperature steam and carbon dioxide. Yet another attractive alternative process for producing synthesis gas is the auto-thermal reformer (ATR) process which uses oxidation to produce heat with a catalyst to permit reforming to occur at lower temperatures than the POx process. However, similar to the POx process, the ATR process requires oxygen to partially oxidize natural gas in a burner to provide heat, as well as high temperature carbon dioxide and steam to reform the residual methane. Normally some steam needs to be added to the natural gas to control carbon formation on the catalyst. However, both the ATR as well as POx processes require an air separation unit (ASU) to produce high-pressure oxygen, which adds complexity as well as capital and operating cost to the overall process.

When the feedstock contains significant amounts of heavy hydrocarbons, the SMR and ATR processes are typically preceded by a pre-reforming step. Pre-reforming is a catalyst based process for converting higher hydrocarbons to methane, hydrogen, carbon monoxide and carbon dioxide. The reactions involved in pre-reforming are typically endothermic. Most pre-reformers operate adiabatically, and thus the pre-reformed feedstock typically leaves at a much lower temperature than the feedstock entering the pre-reformer. Another process that will be discussed in this invention is the secondary reforming process, which is essentially an ATR type process that is fed the product from a steam methane reforming process. Thus, the feed to a secondary reforming process is primarily synthesis gas from steam methane reforming. Depending on the end application, some natural gas may bypass the SMR process and be directly introduced into the secondary reforming step. Also, when a SMR process is followed by a secondary reforming process, the SMR may operate at a lower temperature, e.g. 650° C. to 825° C. versus 850° C. to 1000° C.

As can be appreciated, the conventional methods of producing a synthesis gas such as have been discussed above are expensive and require complex installations. To overcome the complexity and expense of such installations it has been proposed to generate the synthesis gas within reactors that utilize an oxygen transport membrane to supply oxygen and thereby generate the heat necessary to support endothermic heating requirements of the reforming reactions. A typical oxygen transport membrane has a dense layer that, while being impervious to air or other oxygen containing gas will transport oxygen ions when subjected to an elevated operational temperature and a difference in oxygen partial pressure across the membrane.

Examples of oxygen transport membrane based reforming systems used in the production of synthesis gas can be found in U.S. Pat. Nos. 6,048,472; 6,110,979; 6,114,400; 6,296,686; and 7,261,751. There is an operational problem with some or all of these oxygen transport membrane based systems because such oxygen transport membranes need to operate at high temperatures of around 900° C. to 1100° C. Where hydrocarbons such as methane and higher order hydrocarbons are subjected to such high temperatures within the oxygen transport membrane, excessive carbon formation occurs, especially at high pressures and low steam to carbon ratios. The carbon formation problems are particularly severe in the above-identified prior art oxygen transport membrane based systems. A different approach to using an oxygen transport membrane based reforming system in the production of synthesis gas is disclosed in U.S. Pat. No. 8,349,214 which provides a oxygen transport membrane based reforming system that uses hydrogen and carbon monoxide as part of the reactant gas feed to the oxygen transport membrane tubes and minimizes the hydrocarbon content of the feed entering the permeate side of the oxygen transport membrane tubes. Excess heat generated within the oxygen transport membrane tubes is transported mainly by radiation to the reforming tubes made of conventional materials. Use of low hydrocarbon content high hydrogen and carbon monoxide feed to the oxygen transport membrane tubes addresses many of the highlighted problems with the earlier oxygen transport membrane systems.

There is a continuing need to improve the efficiency and cost-effectiveness of production of liquid hydrocarbon products from a Fischer-Tropsch process. Accordingly, there is a specific need to identify and develop advanced technologies that will improve the efficiency and reduce the cost of producing synthesis gas for use in applications for producing liquid fuels, as well as improving or customizing the characteristics of synthesis gas for such applications.

SUMMARY OF THE INVENTION

The present invention in one or more aspects can be characterized as a method for producing a synthesis gas in an oxygen transport membrane based reforming system configured for use in a Fischer-Tropsch or Fischer-Tropsch type process. Examples of oxygen transport membrane based reforming systems employable in the present invention are described in U.S. patent application Ser. Nos. 14/078,897, 14/508,297, 14/508,326, and 14/508,344, which are all incorporated herein by reference. In one embodiment the method comprising the steps of: (i) reforming a feed stream in a reforming reactor in the presence of steam, heat and a reforming catalyst disposed in the reforming reactor to produce a reformed synthesis gas stream comprising hydrogen, carbon monoxide, and unreformed hydrocarbon gas; and (ii) further reforming the reformed synthesis gas stream in the presence of one or more catalysts contained in an oxygen transport membrane based reforming reactor, reaction products and heat to produce a synthesis gas product stream; wherein a portion of the heat required for the reforming of the feed stream is transferred via radiation from the oxygen transport membrane based reforming reactor which is disposed proximate the reforming reactor; and wherein the feed stream comprises a methane containing feed and a tail gas feed wherein the tail gas feed is produced in the Fischer-Tropsch process. The synthesis gas product stream is converted into a liquid hydrocarbon product and a Fischer-Tropsch tail gas using a Fischer Tropsch process or Fischer Tropsch type process. The step of further reforming the reformed synthesis gas stream further comprises: (a) feeding the reformed synthesis gas stream to a reactant side of a reactively driven and catalyst containing oxygen transport membrane based reforming reactor, wherein the oxygen transport membrane based reforming reactor includes at least one oxygen transport membrane element configured to separate oxygen from an oxygen containing stream at an oxidant side of the reactively driven and catalyst containing oxygen transport membrane reforming reactor to the reactant side through oxygen ion transport when subjected to an elevated operational temperature and a difference in oxygen partial pressure across the at least one oxygen transport membrane element; (b) reacting a portion of the reformed synthesis gas stream at the reactant side of the reactively driven and catalyst containing oxygen transport membrane based reforming reactor with oxygen permeated through the at least one oxygen transport membrane element to produce the difference in oxygen partial pressure across the at least one oxygen transport membrane element, reaction products, and heat, including the radiant heat transferred to the reforming reactor for the reforming of the feed stream; and (c) reforming the unreformed hydrocarbon gas in the reformed synthesis gas stream in the oxygen transport membrane based reforming reactor in the presence of the catalysts, the reaction products and the heat to produce the synthesis gas product stream.

The present invention may also be characterized as a method for producing a liquid hydrocarbon product from a Fischer-Tropsch or Fischer-Tropsch type process, the method comprising the steps of: (i) reforming a feed stream in a reforming reactor in the presence of steam, heat and a reforming catalyst disposed in the reforming reactor to produce a reformed synthesis gas stream comprising hydrogen, carbon monoxide, and unreformed hydrocarbon gas; (ii) further reforming the reformed synthesis gas stream in the presence of one or more catalysts contained in an oxygen transport membrane based reforming reactor, reactions products and heat to produce a synthesis gas product stream; and (iii) synthesizing the synthesis gas product stream using a Fischer Tropsch process to produce the liquid hydrocarbon product and a Fischer-Tropsch tail gas. A portion of the heat required for the reforming of the feed stream in the reforming reactor is transferred via radiation from the oxygen transport membrane based reforming reactor which is disposed proximate the reforming reactor and the feed stream comprises a methane containing feed and a portion of the Fischer-Tropsch tail gas. The step of further reforming the reformed synthesis gas stream further comprises: (a) feeding the reformed synthesis gas stream to a reactant side of a reactively driven and catalyst containing oxygen transport membrane based reforming reactor, wherein the oxygen transport membrane based reforming reactor includes at least one oxygen transport membrane element configured to separate oxygen from an oxygen containing stream at an oxidant side of the reactively driven and catalyst containing oxygen transport membrane reforming reactor to the reactant side through oxygen ion transport when subjected to an elevated operational temperature and a difference in oxygen partial pressure across the at least one oxygen transport membrane element; (b) reacting a portion of the reformed synthesis gas stream at the reactant side of the reactively driven and catalyst containing oxygen transport membrane based reforming reactor with oxygen permeated through the at least one oxygen transport membrane element to produce the difference in oxygen partial pressure across the at least one oxygen transport membrane element, reaction products, and heat, including the radiant heat transferred to the reforming reactor for the reforming of the feed stream; and (c) reforming the unreformed hydrocarbon gas in the reformed synthesis gas stream in the oxygen transport membrane based reforming reactor in the presence of the catalysts, the reaction products and the heat to produce the synthesis gas product stream.

In all embodiments of the above-described methods, the ratio of H2/CO in the synthesis gas product stream is about 1.7 to about 2.9, and in another embodiment from about 1.9 to about 2.2. To achieve this relatively low H2/CO ratio, the feed stream generally comprises from about 20% to about 45% by volume of the tail gas feed and from about 55% to about 80% by volume of the methane containing feed. About 50% to about 80% by volume of the tail gas produced in the Fischer-Tropsch process is diverted to obtain the desired feed stream. Optionally the feed stream can be formed to also contain a hydrogen gas feed wherein the hydrogen gas feed is at most 20% by volume of the feed stream. An optional feature or process step in the above described methods is the diversion of a portion of the synthesis gas product stream to a hydrogen separation membrane to produce a synthesis gas stream with lower H2/CO ratio (also referred to as a carbon monoxide rich stream) and a hydrogen rich permeate. In the preferred embodiments, less than about 25% of the synthesis gas product stream is diverted to the hydrogen separation membrane. The synthesis gas with lower H2/CO ratio exiting the hydrogen separation membrane is then recombined with the synthesis gas product stream to produce a conditioned synthesis gas stream wherein the conditioned synthesis gas stream has a H2/CO ratio of about 1.7 to about 2.2. A portion of the hydrogen rich stream, typically after some compression, may be directed to the feed stream. Alternatively for the case of multi-stage reactors in the Fischer-Tropsch section, a portion of the hydrogen-rich stream may be used to increase the H2/CO ratio of the synthesis gas feed to the second or subsequent stage of Fischer-Tropsch synthesis. This portion of the hydrogen rich stream could also be upgraded to high purity H2 in a pressure swing adsorption unit (PSA), which would generate a hydrogen-containing tail gas as byproduct. High purity H2 could be used in Fischer-Tropsch synthesis as described above and/or used in the final upgrading step that converts Fischer-Tropsch liquids to finished products.

In all embodiments of the above-described methods the synthesis gas product stream from the oxygen transport membrane based reforming system is fed to a Fischer-Tropsch process also referred to as a Fischer-Tropsch type process to produce at least a hydrocarbon liquid product and a Fischer-Tropsch tail gas by product. The Fischer-Tropsch process employs a Fischer-Tropsch reactor selected from the group consisting essentially of a fixed bed reactor, a slurry phase reactor, a synthol reactor, or a microchannel reactor. The Fischer-Tropsch process can be configured as a multi-stage Fischer-Tropsch process comprising two or more Fischer-Tropsch reactors and a portion of the hydrogen-rich stream is fed to one or more of the Fischer-Tropsch reactors.

BRIEF DESCRIPTION OF THE DRAWINGS AND TABLES

The above and other aspects, features, and advantages of the present invention will be more apparent from the following, more detailed description thereof, presented in conjunction with the following drawings and Tables, in which.

Figure 1:
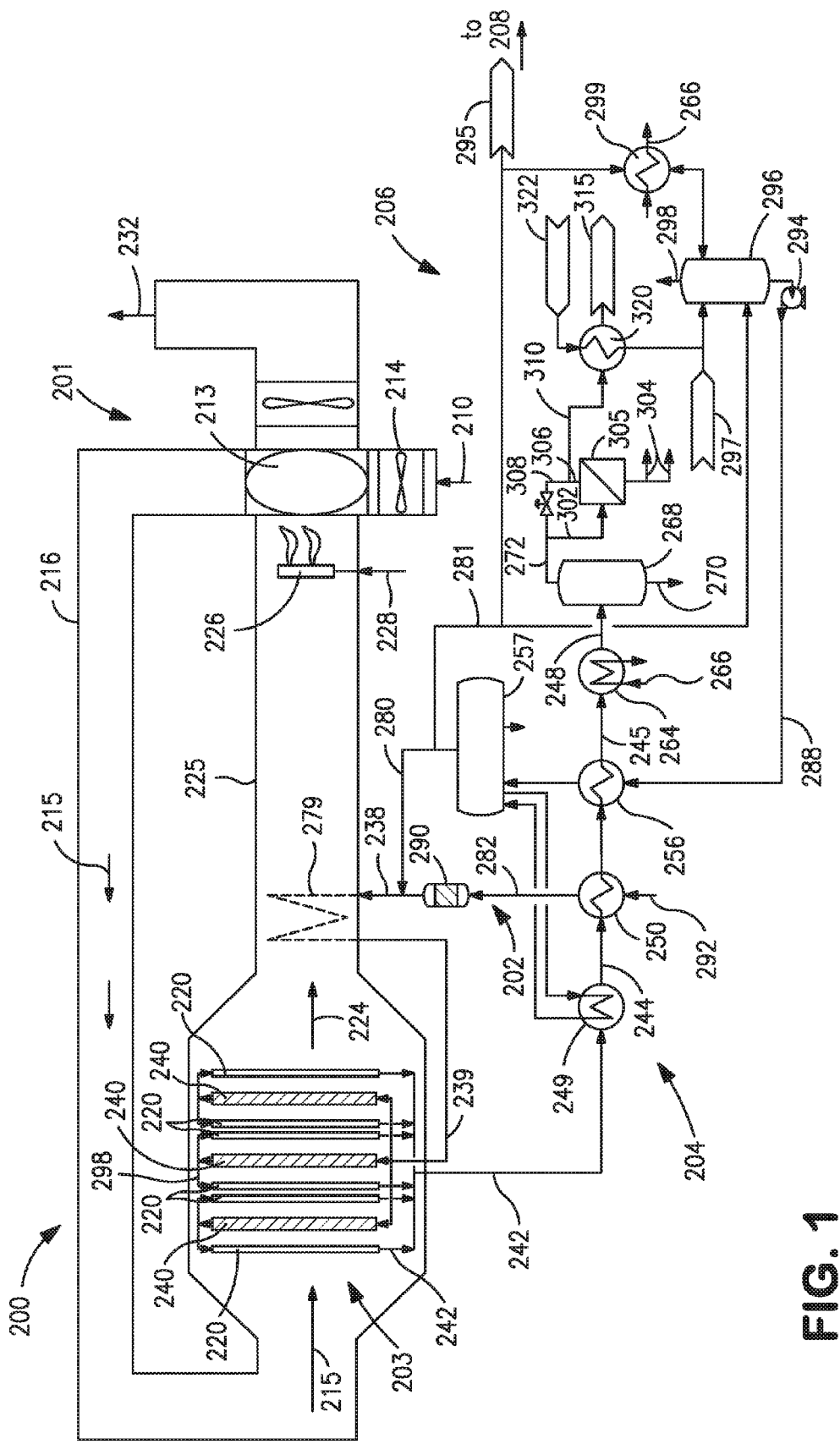
FIG. 1 shows a schematic illustration of a synthesis gas island comprising an oxygen transport membrane based reforming reactor suitable for use in the present method and system.

FIG. 3 presents modeled data showing the targeted process and operating conditions using the system of FIG. 1 for a mixed feed stream having a steam to carbon ratio of 1.5; an oxygen transport membrane based reforming reactor pressure of 460 psia; an oxygen transport membrane based reforming reactor exit temperature of 1800° F.; a fixed output of liquid hydrocarbon products of about 400 barrels per day and a varying percentage of Fischer-Tropsch tail gas added to the mixed feed stream;

FIG. 4 presents modeled data showing the composition of the synthesis gas fed to the Fischer-Tropsch process for the process conditions described with reference to FIG. 3 using the system of FIG. 1 for a mixed feed stream having a steam to carbon ratio of 1.5; an oxygen transport membrane based reforming reactor pressure of 460 psia; an oxygen transport membrane based reforming reactor exit temperature of 1800° F.; and a varying percentage of Fischer-Tropsch tail gas added to the mixed feed stream;

FIG. 5 presents modeled data showing the targeted process and operating conditions using the system of FIG. 1 for a mixed feed stream having a steam to carbon ratio of 2.0; an oxygen transport membrane based reforming reactor pressure of 460 psia; an oxygen transport membrane based reforming reactor exit temperature of 1800° F.; a fixed output of liquid hydrocarbon products of about 400 barrels per day and a varying percentage of Fischer-Tropsch tail gas added to the mixed feed stream; and FIG. 6 presents modeled data showing the composition of the synthesis gas fed to the Fischer-Tropsch process for the process conditions described with reference to FIG. 5 using the system of FIG. 1 for a mixed feed stream having a steam to carbon ratio of 2.0; an oxygen transport membrane based reforming reactor pressure of 460 psia; an oxygen transport membrane based reforming reactor exit temperature of 1800° F.; and a varying percentage of Fischer-Tropsch tail gas added to the mixed feed stream.

DETAILED DESCRIPTION

Figure 2:
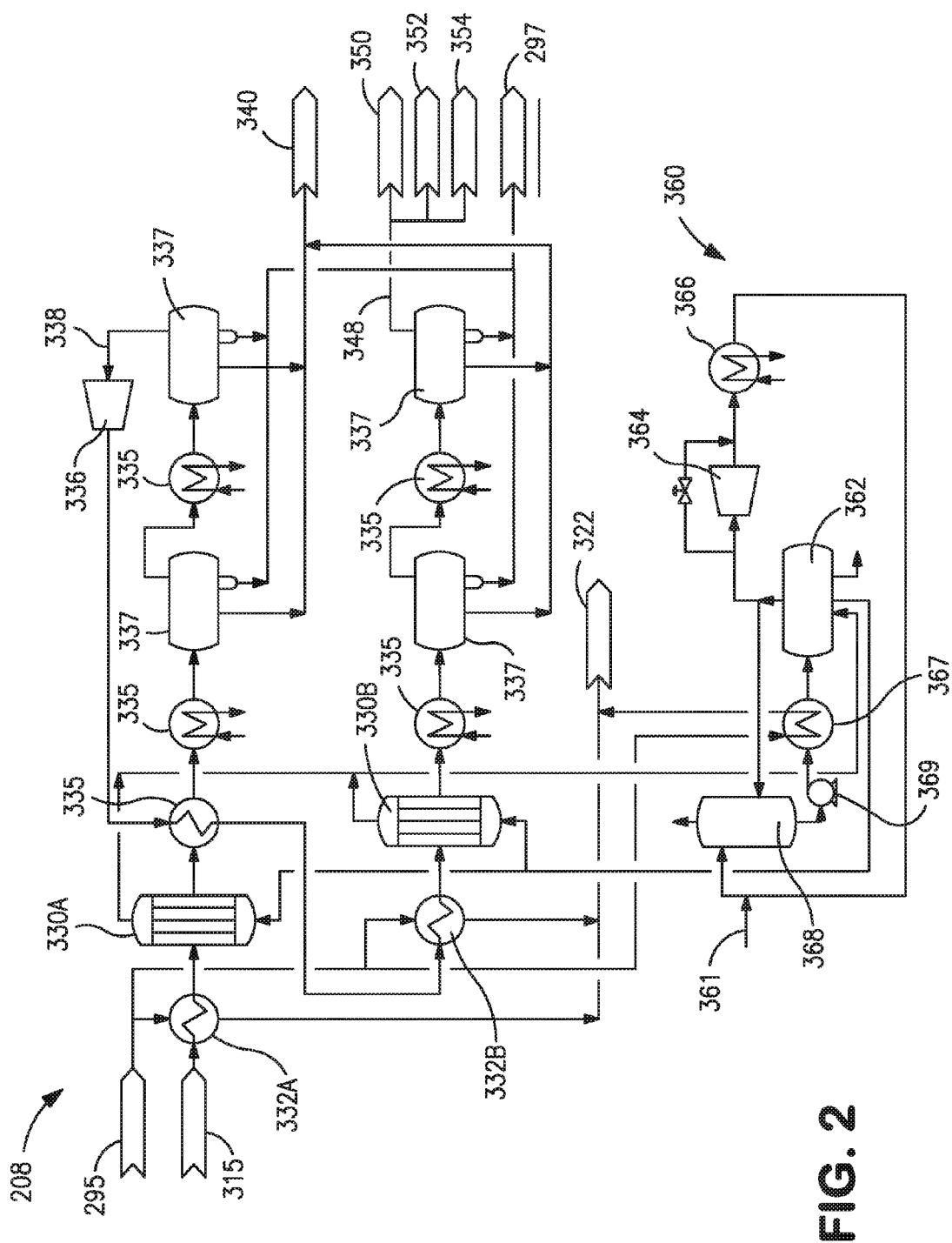
FIG. 2 shows a schematic illustration of a Fischer-Tropsch process island employing a recycle circuit of the Fischer-Tropsch tail gas to the synthesis gas island and that is suitable for use in the present method and system.

FIGS. 1 and 2 provide schematic illustrations of the present system and method for producing liquid hydrocarbon products via a Fischer-Tropsch process using synthesis gas produced from an oxygen transport membrane based reforming subsystem. The illustrated system 200 preferably includes: (i) an air supply and preheating subsystem 201; (ii) a reforming feed and conditioning subsystem 202; (iii) an oxygen transport membrane based reforming subsystem 203; (iv) a heat recovery subsystem 204; (v) a synthesis gas conditioning subsystem 206; and (vi) a Fischer-Tropsch synthesis subsystem 208. As described in more detail below, the various subsystems are fluidically integrated in a manner that improves the overall efficiency and cost-effectiveness of liquid hydrocarbon production. In particular, the tail gas from the Fischer-Tropsch process is recycled and optionally used as both a supplemental fuel as well as part of the feed stream in the synthesis gas production.

The air supply and preheating subsystem includes a source of feed air or other oxygen containing feed stream 210; a continuously rotating regenerative air preheater 213 configured to heat the source of feed air 210; and conduits 216 for supplying the heated feed air stream 215 from the regenerative air preheater 213 to the oxygen transport membrane based reforming subsystem 203. The air supply and preheat subsystem further includes return conduits 225 configured to return the heated, oxygen depleted air stream 224 from the oxygen transport membrane based reforming subsystem to the regenerative air preheater (e.g. ceramic regenerator) 213 to heat the source of feed air 210 and subsequently exhaust the cooled oxygen depleted stream as exhaust stream 232.

An oxygen containing stream 210, such as air, is preferably introduced to the system by means of a forced draft (FD) fan 214 into a high efficiency, cyclic, continuously rotating ceramic regenerative air preheater 213 disposed in operative association with the incoming air or oxygen containing feed stream 210 and the heated retentate stream 224 exiting the reforming subsystem for purposes of preheating the incoming air or oxygen containing feed stream 210. The ceramic regenerator 213 heats the incoming air feed stream 210 to a temperature in the range of from about 850° C. to about 1000° C.

The heated feed air stream 215 is directed to the oxidant-side of the oxygen transport membrane based reforming subsystem 203, and more particularly to the oxidant-side of the oxygen transport membrane elements or tubes 220 within the oxygen transport membrane based reforming subsystem 203. As the heated feed air stream 215 flows across the oxidant-side surfaces of the oxygen transport membrane elements or tubes 220, oxygen ions from the heated feed air stream permeate through the oxygen transport membrane elements or tubes 220 to the reactant side of the oxygen transport membrane elements or tubes 220. The oxygen ions recombine at the permeate side of the oxygen transport membrane elements or tubes 220 and react with a hydrogen containing stream 298 at the permeate side to create the heat and a difference in oxygen partial pressure across the oxygen transport membrane element 220 which drives the oxygen transport.

As a result of the reactively driven oxygen ion transport across the membranes, the feed air stream 215 becomes generally depleted of oxygen and heated by the convective heat transfer between the oxygen transport membrane elements or tubes 220 and the passing air stream 215. At the high temperatures within the oxygen transport membrane based reforming subsystem 203, approximately 50% or more, in another embodiment 70% or more of the oxygen within the heated feed air stream 215 is transported or permeated across the oxygen transport membrane elements or tubes 220. The oxygen depleted air 224 leaves the oxygen transport membrane reforming subsystem as a heated retentate stream 224 at a higher temperature than the heated air feed stream 215. The heated, oxygen depleted retentate stream 224 is first used to heat the steam containing mixed feed stream 238 to a temperature from about 450° C. and 650° C., in another embodiment to a temperature from about 500° C. and 600° C., and may optionally be used to further heat steam to superheated steam (not shown). It is conceivable that the mixed feed heater 279 and optional steam superheater disposed within the return conduits 225 could alternatively be located in a separate fired heater (not shown). In that case, the fuel requirements of the duct burner described below will be substantially less.

The temperature of this oxygen depleted retentate stream 224 preferably needs to be then increased back to a temperature of from about 1000° C. to about 1200° C. prior to being directed to the ceramic heat exchanger or regenerator 213. This increase in temperature of the oxygen depleted, retentate stream 224 is preferably accomplished by use of a duct burner 226, which facilitates combustion of a supplemental fuel stream 228 using some of the residual oxygen in the retentate stream. In the ceramic heat exchanger or regenerator 213, the re-heated, oxygen depleted retentate stream provides the energy to raise the temperature of the incoming feed air stream 210 from ambient temperature to a temperature of from about 850° C. to about 1050° C. The resulting cold retentate stream exiting the ceramic heat exchanger, typically containing less than 5% oxygen is exhausted at a temperature of around 150° C. as exhaust stream 232. Alternatively, the duct burner 226 may be disposed directly in the air intake duct 216 downstream of the continuously rotating ceramic regenerator 213 to further pre-heat the incoming feed air stream 210. Such an arrangement would allow use of a smaller regenerator and less severe operating conditions. It may also enable the use of a regenerator with conventional materials instead of ceramics. The supplemental fuel stream 228 can be a source of natural gas or a portion of the tail gas routed from elsewhere in the plant or a combination thereof. As described in more detail below, the preferred tail gas is typically associated with the Fischer-Tropsch synthesis subsystem.

The reforming feed and conditioning subsystem 202 is configured to include a feed conditioning section. More particularly, the feed stream 292 to be reformed in the oxygen transport membrane based reforming subsystem 203 is typically natural gas or associated gas based feed that is mixed with a portion of the Fischer-Tropsch tail gas and optionally a small amount of hydrogen or hydrogen-rich gas. Preferably, the feed stream 292 comprises from about 20% to about 45% by volume of the Fischer-Tropsch tail gas and from about 55% and 80% by volume of the methane containing feed (i.e. natural gas or associated gas). As shown in FIG. 1 the feed stream 292 is preheated, if necessary, in a preheater 250 to a temperature of from about 300° C. to about 400° C. Since natural gas typically contains unacceptably high level of sulfur species, a small amount of hydrogen or hydrogen-rich gas, is added to the natural gas feed stream to facilitate desulfurization. Preferably, the heated feed stream 282 undergoes a sulfur removal process via device 290 such as hydro-treating unit to reduce the sulfur species to $H_2S$, which is subsequently removed in a guard bed using material like ZnO or CuO. The hydrotreating step also saturates any alkenes present in the hydrocarbon containing feed stream. Alternately the feed stream 292 can be formed by first desulfurizing the methane containing feed, i.e. natural gas or associated gas in the hydrotreating unit 290 and then mixing the resulting desulfurized methane containing feed with a portion of the Fischer-Tropsch tail gas.

Saturated steam, or in another embodiment superheated steam 280 is then preferably added to the desulfurized and conditioned feed stream, as required, to produce a steam containing mixed feed stream 238 having a steam to carbon ratio of from about 1.0 to about 2.5, and more preferably from about 1.2 to about 2.2. The steam 280 is preferably from about 15 bar to about 80 bar and from about 300° C. to about 600° C. and may be generated in a fired heater (not shown) using a source of process steam or diverted from other portions of the system. The resulting steam containing mixed feed stream 238 is heated by means of indirect heat exchange with the heated retentate stream 224 to produce a heated mixed feed stream 239 at a temperature of from about 300° C. to about 650° C. and in another embodiment to a temperature of from about 450° C. to about 600° C.

Further, since the natural gas or associated gas based feed stream generally contains some higher hydrocarbons that will break down at high temperatures to form unwanted carbon deposits that adversely impact the reforming process, the steam containing mixed feed stream 239 may optionally be pre-reformed in an adiabatic pre-reformer. Although not shown in the illustrated embodiment, the pre-reformer converts the higher hydrocarbons present in the feed stream to methane, hydrogen, carbon monoxide, and carbon dioxide. An alternative pre-reformer suitable for use with the present embodiments would be a heated pre-reformer that is thermally coupled with the oxygen transport membrane based reforming subsystem. The pre-reformed feed stream is then directed to the oxygen transport membrane based reforming reactor, as described in the paragraphs that follow.

The oxygen transport membrane based reforming subsystem 203 generally comprises two reactors that can be in the form of sets of catalyst containing tubes—reforming reactor and oxygen transport membrane reactor. As seen in FIG. 1, the OTM Combined Reforming Reactor comprises two reactor sections. A first reforming reactor section preferably consists of a plurality of reforming tubes 240 where the initial or primary reforming occurs. A second reactor section, namely an oxygen transport membrane based reactor, consists of catalyst containing oxygen transport membrane elements or tubes 220 where secondary reforming of the partially reformed stream occurs. Although only six secondary reforming oxygen transport membrane tubes 220 are illustrated in close proximity to three primary reforming tubes 240, as would occur to those skilled in the art, there could be many of such secondary reforming oxygen transport membrane tubes and many primary reforming tubes in each OTM based reforming subsystem. Likewise, there could be multiple OTM subsystems in an industrial application of the OTM technology.

The heated air feed stream 215 is directed via an intake duct 216 to a plurality of catalyst containing oxygen transport membrane tubes 220 having an oxidant side and a reactive side that is capable of conducting oxygen ions at an elevated operational temperature. The oxidant side of the secondary reforming oxygen transport membrane tubes 220 is preferably the exterior surface of the ceramic tubes exposed to the heated oxygen containing stream and the reactant side or permeate side is preferably the interior surface of the ceramic tubes. Within each of the secondary reforming oxygen transport membrane tubes 220 are one or more catalysts that facilitate partial oxidation and reforming.

The heated mixed feed stream 239 first passes through the reforming tubes 240, which contain conventional reforming catalyst which reforms a portion of the natural gas based stream 239. The temperature of the partially reformed hydrogen-rich synthesis gas 298 leaving the reforming tubes is designed to be at a temperature of from about 650° C. to about 850° C. This partially reformed synthesis gas 298 is then fed to the oxygen transport membrane tubes 220 that are also filled with one or more catalysts, which facilitate further reforming and partial oxidation. Oxygen from the heated intake or feed air 215 permeates through the oxygen transport membrane tubes 220 and facilitates a reaction between the permeated oxygen and a portion of the hydrogen and carbon monoxide within the partially reformed synthesis gas 298 at the reactant side of the oxygen transport membrane tubes 220. A portion of the energy or heat generated by this reaction is used for in-situ secondary reforming or further reforming of the residual methane in the partially reformed synthesis gas 298. The rest of the energy or heat is transferred by radiation to the reforming tubes 240 to drive the primary reforming reactions in the reforming reactor and by convection to the oxygen-depleted retentate stream. The synthesis gas 242 leaving the oxygen transport membrane tubes 220 is at a temperature of from about 900° C. to about 1050° C.

As described in more detail in U.S. patent application Ser. No. 14/078,897, which is incorporated herein by reference, the produced synthesis gas stream generally contains hydrogen, carbon monoxide, unconverted methane, steam, carbon dioxide and other constituents (See Tables). A significant portion of the sensible heat from the produced synthesis gas stream can be recovered using a heat recovery subsystem 204 designed to cool the produced synthesis gas stream 242 while preheating the natural gas based feed stream 292 and boiler feed water 288 as well as generating process steam 281.

As shown in FIG. 1, the hot synthesis gas 242 exiting the oxygen transport membrane based reforming reactor is directly cooled to about 400° C. or less in a process gas (PG) boiler 249 operatively associated with the process stream drum 257. The temperature is selected to minimize metal dusting issues. The initially cooled synthesis gas stream 244 is then used to preheat the mixed or conditioned feed stream 292 comprising the natural gas feed, the Fischer-Tropsch tail gas feed, and the hydrogen feed in a feed pre-heater 250. Downstream of the feed pre-heater, the synthesis gas pre-heats boiler feed water 288 in an economizer 256. Synthesis gas 245 leaving the economizer 256 is further cooled using synthesis gas cooler 264 fed by a cooling water stream 266. A fin-fan air cooler (not shown) can be added ahead of the synthesis gas cooler 264 to minimize cooling water requirements. The cooled synthesis gas 248 then enters a knock-out drum 268 where water is removed from the bottoms as a process condensate stream 270 which, although not shown, can be recycled for use as feed water, and the cooled synthesis gas 272 is recovered overhead. In the illustrated embodiment, the feed water is sent from a plurality of sources via heat exchangers 299, 320 to a de-aerator 296 that is configured to supply the boiler feed water and eventually the process steam 281 while exhausting a vent gas 298. The boiler feed water 288 is preferably pumped from the de-aerator via pump 294, further heated in the economizer 256 and sent to the process steam drum 257. As can be appreciated by those skilled in the art, the illustrated heat recovery subsystem operatively couples or integrates the water and steam requirements of the synthesis gas production (i.e. synthesis gas island) with the Fischer-Tropsch liquid production. For example, the excess steam 295 produced in PG boiler 249 can be used to pre-heat the feed streams in the Fischer-Tropsch section 208 (see FIG. 2) as shown in heat exchangers 332A and 332B. The condensed steam 322 and process water 297 generated in the Fischer-Tropsch section 208 are then returned to the de-aerator 296 (see FIG. 1).

The present system also includes a synthesis gas conditioning subsystem 206. In the illustrated embodiment, the synthesis gas conditioning subsystem 206 is configured to optionally divert a portion of the cooled synthesis gas 302 to a hydrogen separation membrane 305 to produce a hydrogen rich permeate 304 and a synthesis gas stream 306 with lower H2/CO ratio. Up to 25% of the synthesis gas may be diverted to the hydrogen separation membrane 305. The exact amount depends on many process variables and operating conditions, such as synthesis gas composition, temperature, pressure, etc. For example, during start-up of the system 200, a significant volume of the synthesis gas may need to be diverted to the hydrogen separation membrane 305 until the Fischer-Tropsch section has reached a steady operating point and sufficient flow of Fischer-Tropsch tail gas has been established, which can be recycled back to the reforming feed stream.

The main purpose of the synthesis gas conditioning subsystem 206 is to adjust, typically reduce, the H2/CO ratio of the synthesis gas 306 to meet the specifications and/or requirements of the Fischer-Tropsch process. This is partially achieved by recombining the synthesis gas stream with lower H2/CO ratio 306 exiting the hydrogen separation membrane 305 with the remaining synthesis gas product stream 308 to produce a conditioned synthesis gas stream 310 having a H2/CO ratio of between about 1.7 to about 2.2. Depending on the operating pressure of the oxygen transport membrane reformer 203, a synthesis gas compressor (not shown) may be required to increase the pressure of the conditioned synthesis gas stream 310 to between about 350 and 450 psia. Also not shown, but known to those skilled in the art, further conditioning of the synthesis gas stream 310 may be required to reduce levels of contaminants such as ammonia, sulfur species and others, to below the threshold specifications for the catalysts used in the downstream Fischer-Tropsch reactors. The conditioned synthesis gas is subsequently cooled in synthesis gas cooler 320 and the final synthesis gas product 315 is directed to the Fischer-Tropsch process.

In addition, a portion of the hydrogen rich stream 304A exiting the hydrogen separation membrane 305 may be used as a source of supplemental fuel or directed to the reformer feed stream to facilitate desulfurization of natural gas. Another portion of the hydrogen-rich stream 304B may be optionally fed to one or more of Fischer-Tropsch reactors where the supplemental hydrogen is used to adjust the H2/CO ratio of the synthesis gas feed to the Fischer-Tropsch reactors in the second or subsequent stages in a multi-stage Fischer-Tropsch process. Alternatively, 304B could be further upgraded to a high purity hydrogen stream using a pressure swing adsorption (PSA) system. This high purity hydrogen could be used in the Fischer-Tropsch process as described above and/or used in the product upgrading section to convert the Fischer-Tropsch liquids to finished products. An embodiment of the Fischer-Tropsch synthesis subsystem 208 is shown in FIG. 2 as a multi-stage synthesis process with interstage compression of the intermediate product stream 338 using an interstage compressor 336. Embodiments with a single stage or more than two stages are also possible. As seen therein, the conditioned synthesis gas stream 315 is synthesized into selected liquid hydrocarbon products in accordance with the general reaction '2H$_2$+CO→—CH2-+H$_2$O' in a Fischer-Tropsch catalyst based reactors 330A and 330B (e.g. fixed bed reactors, slurry phase reactors, synthol reactors, or microchannel reactors) and subsequently purified into a final liquid hydrocarbon product 340 in a manner generally known to those skilled in the art. The liquid hydrocarbon product 340 generally produced by the Fischer-Tropsch gas to liquid (GTL) synthesis process heavily depends on temperature, catalyst, pressure and, more importantly, the synthesis gas composition. Typical FT processes include the use of preheaters 332A and 332B to heat the feed streams to each of the FT reactors using process steam 295 as well as a plurality of coolers 335 and separators 337. The illustrated system further includes a separate steam processing section 360, with steam drum 362, steam turbine 364, turbine condenser 366, deaerator 368, pump 369, heat exchanger 367, and boiler feedwater make-up 361. The steam in steam processing section 360 is generated by the steam cooled reactors 330A and 330B. Although not explicitly shown, in some instances it may be preferable to superheat the saturated steam being generated in this section prior to sending to the steam turbine. A possible location for this steam superheater could be in the return conduit 225 of the OTM reforming system.

For example, at high temperature Fischer-Tropsch reactions (i.e. 330° C.-350° C.) the liquid hydrocarbon product predominantly comprises gasoline and light olefins whereas at low temperature Fischer-Tropsch reactions (i.e. 220° C.-250° C.) the liquid hydrocarbon product predominantly comprises distillates and waxes, with some gasoline. Catalysts used in many Fischer-Tropsch gas to liquid (GTL) synthesis processes include cobalt-based catalysts or iron-based catalysts. The synthesis gas composition, and in particular, the ratio of hydrogen to carbon monoxide ($H_2$/CO ratio) is an important variable that affects the Fischer-Tropsch gas to liquid (GTL) synthesis process and can be controlled by aspects and features of the present invention. For Fischer-Tropsch reactors using iron-based catalyst, the target H2/CO ratio is around 1:1. For Fischer-Tropsch reactors using cobalt-based catalyst, the preferred embodiment for this invention, the target H2/CO ratio is around 2:1. The Fischer-Tropsch synthesis section 208 also generates a tail gas 348 comprising unconverted carbon monoxide, hydrogen, and water as well as light hydrocarbons such as methane and/or $C_2$-$C_5$ hydrocarbons. A portion of the Fischer-Tropsch tail gas 350 is recycled to the reforming feed and conditioning subsystem 202 where it is mixed with the natural gas feed to be reformed in the oxygen transport membrane based reforming subsystem 203. Another portion of the Fischer-Tropsch tail gas 352 can be used as a supplemental fuel source for the duct burner in the air intake subsystem 201 or other sections of the synthesis gas island. Any Fischer-Tropsch tail gas 354 that is not used elsewhere in the disclosed system 200 may be used for power generation or flared. One way to minimize the amount of unutilized or flared Fischer-Tropsch tail gas 354 and improve the overall process is to increase the steam to carbon ratio of the mixed feed stream 238.

As indicated above, the H2/CO ratio in the synthesis gas product stream 315 is preferably from about 1.7 to about 2.9, and in another embodiment from about 1.9 to about 2.2. To achieve this relatively low H2/CO ratio in the synthesis gas product stream 315, the feed stream generally comprises from about 20% to about 45% by volume of the Fischer-Tropsch tail gas 350 and from about 55% to about 80% by volume of the methane containing feed. Put another way, the amount of Fischer-Tropsch tail gas 350 and 352 recycled or diverted back to the oxygen transport membrane based synthesis gas production is from about 50% to about 80% by volume of the tail gas 348 produced in the Fischer-Tropsch process. The rest of the FT tail gas can be used as fuel in the overall process, e.g. fuel stream 226 to the duct burner 228, or potentially recycled back to the FT reactors.

EXAMPLES

FIG. 3 shows a modeled comparison of the targeted process and operating conditions using the system of FIG. 1 for a mixed feed stream having a steam to carbon ratio of 1.5; an oxygen transport membrane based reactor pressure of 460 psia; an oxygen transport membrane based reforming exit temperature of 1800° F.; and a fixed output of liquid hydrocarbon products of about 400 barrels per day. The amount of recycled Fischer-Tropsch tail gas added to the mixed feed stream is varied from 0% to 80% of the Fischer-Tropsch tail gas generated.

As seen in FIG. 3, for the same liquid production of about 400 barrels per day, the presently disclosed system and process provides clear cost and performance advantages. For example, the total natural gas required per barrel of FT product is 15330 scf per barrel with 0% recycle of the Fischer-Tropsch tail gas to the mixed feed stream but is only 10172 scf per barrel with 80% recycle of the Fischer-Tropsch tail gas to the mixed feed stream. This represents a reduction in natural gas consumption of over 33% by recycling most of the Fischer-Tropsch tail gas back to the reforming feed stream. In addition, the quality of the synthesis gas, as characterized by the H2/CO ratio (pre-membrane), is improved from 2.969 (at 0% recycle) to about 1.902 when 80% of the Fischer-Tropsch tail gas is recycled back to the reforming feed stream. Synthesis gas flow to the membrane decreases from 41% of total synthesis gas produced at 0% recycle to less than 15% at recycle rates of 60% or higher. Synthesis gas flow to membrane is not required when more than 74% of the tail gas is recycled back to the reforming feed stream. There are other advantages such as lower oxygen utilization, lower air utilization, lower steam to process rate, lower hydrogen separation, and lower power requirement as the amount of recycled Fischer-Tropsch tail gas is increased as can be seen in FIG. 3.

FIG. 4 presents modeled data showing the composition of the synthesis gas fed to the Fischer-Tropsch process for the process and operating conditions described with reference to FIG. 3 using the system of FIG. 1 for a mixed feed stream having a steam to carbon ratio of 1.5; an oxygen transport membrane based reactor pressure of about 460 psia; an oxygen transport membrane based reactor exit temperature of 1800° F.; and a varying percentage of Fischer-Tropsch tail gas added to the mixed feed stream.

FIG. 5 shows another modeled comparison of the targeted process and operating conditions using the system of FIG. 1 for a mixed feed stream having a steam to carbon ratio of 2.0; an oxygen transport membrane based reforming reactor pressure of about 460 psia; an oxygen transport membrane based reforming reactor exit temperature of 1800° F.; and a fixed output of liquid hydrocarbon products of about 400 barrels per day. As with FIG. 3, the amount of recycled Fischer-Tropsch tail gas added to the mixed feed stream is varied from 0% to 80% of the Fischer-Tropsch tail gas generated.

As seen in FIG. 5, for the same liquid production of about 400 barrels per day, the presently disclosed system and process provides clear cost and performance advantages. For example, the total natural gas required per barrel of FT product is 16578 scf per barrel with 0% recycle of the Fischer-Tropsch tail gas to the mixed feed stream but is only 10595 scf per barrel with 80% recycle of the Fischer-Tropsch tail gas to the mixed feed stream. This represents a reduction in natural gas consumption of over 36% by recycling most of the Fischer-Tropsch tail gas back to the reforming feed stream. In addition, the quality of the synthesis gas, as characterized by the H2/CO ratio (pre-membrane), is improved from 3.285 (at 0% recycle) to about 2.052 when 80% of the Fischer-Tropsch tail gas is recycled back to the reforming feed stream. Synthesis gas flow to the membrane decreases from 50% of total synthesis gas produced at 0% recycle to less than 15% at recycle rates of 70% or higher. Synthesis gas flow to membrane is not required when more than 79% of the tail gas is recycled back to the reforming feed stream. There are other advantages such as lower oxygen utilization, lower air utilization, lower steam to process rate, lower hydrogen separation, and lower power requirement as the amount of recycled Fischer-Tropsch tail gas is increased as can be seen in FIG. 5.

FIG. 6 presents modeled data showing the composition of the synthesis gas fed to the Fischer-Tropsch process for the process and operating conditions described with reference to FIG. 4 using the system of FIG. 1 for a mixed feed stream having a steam to carbon ratio of 2.0; an oxygen transport membrane based reactor pressure of about 460 psia; an oxygen transport membrane based reactor exit temperature of 1800° F.; and a varying percentage of Fischer-Tropsch tail gas added to the mixed feed stream.

While the inventions herein disclosed have been described by means of specific embodiments and processes associated therewith, numerous modifications and variations can be made thereto by those skilled in the art without departing from the scope of the invention as set forth in the appended claims or sacrificing all of its features and advantages.

TABLE 1

| FT Tail Gas to Syngas Process | 0% | 20% | 40% | 60% | 70% | 71% | 72% | 74% | 76% | 78% | 80% |
|---|---|---|---|---|---|---|---|---|---|---|---|
| Natural Gas/Product, scf/bbl* | 15,330 | 14,057 | 12,699 | 11,205 | 10,340 | 10,247 | 10,243 | 10,227 | 10,198 | 10,172 | 10,172 |
| NG to Process, MMSCFD | 6.13 | 5.62 | 5.08 | 4.48 | 4.14 | 4.10 | 4.06 | 3.98 | 3.93 | 3.87 | 3.84 |
| NG to Fuel, MMSCFD | 0.00 | 0.00 | 0.00 | 0.00 | 0.00 | 0.00 | 0.03 | 0.11 | 0.15 | 0.20 | 0.23 |
| Total NG, MMSCFD | 6.13 | 5.62 | 5.08 | 4.48 | 4.14 | 4.10 | 4.10 | 4.09 | 4.08 | 4.07 | 4.07 |
| Air Rate, MMSCFD | 24.73 | 23.57 | 22.30 | 20.79 | 19.90 | 19.79 | 19.69 | 19.47 | 19.30 | 19.13 | 19.06 |
| O2 to OTM, tpd | 137.80 | 131.30 | 124.20 | 115.80 | 110.90 | 110.30 | 109.70 | 108.50 | 107.50 | 106.60 | 106.20 |
| Steam to Process Rate, kpph | 18.12 | 17.43 | 16.60 | 15.32 | 14.57 | 14.53 | 14.49 | 14.32 | 14.17 | 14.04 | 14.11 |
| FT Tail Gas to Process Feed, MMSCFD | 0.00 | 0.67 | 1.40 | 2.23 | 2.72 | 2.78 | 2.83 | 2.95 | 2.87 | 2.75 | 2.82 |
| FT Tail Gas to Fuel, MMSCFD | 0.00 | 0.00 | 0.00 | 0.28 | 1.04 | 1.13 | 1.10 | 1.04 | 0.91 | 0.77 | 0.71 |
| FT Tail Gas to Flare, MMSCFD | 3.28 | 2.70 | 2.10 | 1.20 | 0.12 | 0.00 | 0.00 | 0.00 | 0.00 | 0.00 | 0.00 |
| Total FT Tail Gas. MMSCFD | 3.28 | 3.37 | 3.50 | 3.71 | 3.89 | 3.91 | 3.93 | 3.98 | 3.78 | 3.52 | 3.53 |
| Syngas to H2 Membrane | 40.61% | 34.40% | 26.20% | 14.20% | 5.10% | 3.99% | 2.90% | 0.40% | 0.00% | 0.00% | 0.00% |
| H2 to Fuel/Feed, MMSCFD | 1.68 | 1.62 | 1.57 | 1.20 | 0.41 | 0.32 | 0.23 | 0.03 | 0.00 | 0.00 | 0.00 |
| H2 to Flare, MMSCFD | 2.53 | 1.75 | 0.84 | 0.00 | 0.00 | 0.00 | 0.00 | 0.00 | 0.00 | 0.00 | 0.00 |
| Total H2, MMSCFD | 4.20 | 3.37 | 2.40 | 1.20 | 0.41 | 0.32 | 0.23 | 0.03 | 0.00 | 0.00 | 0.00 |
| Syngas H2:CO Ratio (pre membrane) | 2.97 | 2.80 | 2.60 | 2.36 | 2.20 | 2.19 | 2.17 | 2.13 | 2.07 | 1.98 | 1.90 |
| Stream 315 H2:CO Ratio (Syngas to FT) | 2.13 | 2.13 | 2.13 | 2.13 | 2.13 | 2.13 | 2.13 | 2.13 | 2.07 | 1.98 | 1.90 |
| Power Generated, kW | 466 | 460 | 453 | 448 | 447 | 447 | 446 | 445 | 438 | 430 | 426 |
| Power Required, kW | 466 | 460 | 453 | 448 | 447 | 447 | 446 | 445 | 438 | 430 | 426 |

Steam to carbon ratio: 1.5; OTM outlet pressure: 460 psia; OTM outlet temperature: 1800 F.; FT product rate: 400 BBL/d

TABLE 2

| FT Tail Gas to Syngas Process | 0% | 20% | 40% | 60% | 70% | 71% | 72% | 74% | 76% | 78% | 80% |
|---|---|---|---|---|---|---|---|---|---|---|---|
| Stream 315 (Syngas to FT) Composition (%) | | | | | | | | | | | |
| Hydrogen | 59.618 | 59.266 | 58.773 | 57.962 | 57.316 | 57.231 | 57.153 | 56.964 | 55.991 | 54.721 | 53.337 |
| Nitrogen | 0.363 | 0.412 | 0.490 | 0.636 | 0.775 | 0.794 | 0.814 | 0.858 | 0.929 | 1.017 | 1.109 |
| Water | 0.278 | 0.292 | 0.309 | 0.333 | 0.350 | 0.352 | 0.354 | 0.358 | 0.360 | 0.361 | 0.363 |
| Carbon monoxide | 28.029 | 27.864 | 27.632 | 27.251 | 26.947 | 26.907 | 26.870 | 26.781 | 27.120 | 27.578 | 28.038 |
| Carbon dioxide | 10.008 | 10.641 | 11.481 | 12.736 | 13.682 | 13.801 | 13.912 | 14.174 | 14.785 | 15.567 | 16.452 |
| Methane | 1.701 | 1.523 | 1.313 | 1.080 | 0.929 | 0.913 | 0.895 | 0.863 | 0.811 | 0.755 | 0.700 |
| Ammonia | 0.002 | 0.002 | 0.002 | 0.002 | 0.002 | 0.002 | 0.002 | 0.002 | 0.002 | 0.002 | 0.002 |

Steam to carbon ratio: 1.5; OTM outlet pressure: 460 psia; OTM outlet temperature: 1800 F.; FT product rate: 400 BBL/d

TABLE 3

| FT Tail Gas to Syngas. Process | 0% | 30% | 60% | 70% | 75% | 77% | 78% | 79% | 80% |
|---|---|---|---|---|---|---|---|---|---|
| Natural Gas/Product, scf/bbl | 16,578 | 14,471 | 12,044 | 11,062 | 10,662 | 10,636 | 10,623 | 10,609 | 10,595 |
| NG to Process, MMSCFD | 6.63 | 5.79 | 4.82 | 4.43 | 4.20 | 4.09 | 4.04 | 4.00 | 3.97 |
| NG to Fuel, MMSCFD | 0.00 | 0.00 | 0.00 | 0.00 | 0.07 | 0.16 | 0.21 | 0.25 | 0.27 |
| Total NG, MMSCFD | 6.63 | 5.79 | 4.82 | 4.43 | 4.26 | 4.25 | 4.25 | 4.24 | 4.24 |
| Air Rate, MMSCFD | 27.81 | 25.66 | 23.01 | 21.89 | 21.21 | 20.90 | 20.74 | 20.61 | 20.52 |
| O2 to OTM, tpd | 155.00 | 142.90 | 128.20 | 122.00 | 118.20 | 116.40 | 115.50 | 114.80 | 114.30 |
| Steam to Process Rate, kpph | 26.19 | 24.23 | 21.65 | 20.45 | 19.72 | 19.55 | 19.33 | 19.33 | 19.09 |
| FT Tail Gas to Process Feed, MMSCFD | 0.00 | 1.14 | 2.50 | 3.08 | 3.43 | 3.60 | 3.68 | 3.70 | 3.63 |
| FT Tail Gas to Fuel, MMSCFD | 0.00 | 0.00 | 0.00 | 0.73 | 1.15 | 1.07 | 1.04 | 0.98 | 0.91 |
| FT Tail Gas to Flare, MMSCFD | 3.59 | 2.65 | 1.67 | 0.59 | 0.00 | 0.00 | 0.00 | 0.00 | 0.00 |
| Total FT Tail Gas. MMSCFD | 3.59 | 3.78 | 4.17 | 4.41 | 4.58 | 4.67 | 4.72 | 4.68 | 4.53 |
| Syngas to H2 Membrane | 50.12% | 40.06% | 23.06% | 13.33% | 6.44% | 3.03% | 1.12% | 0.00% | 0.00% |
| H2 to Fuel/Feed, MMSCFD | 2.08 | 1.98 | 1.85 | 1.16 | 0.54 | 0.25 | 0.09 | 0.00 | 0.00 |
| H2 to Flare, MMSCFD | 3.76 | 2.28 | 0.29 | 0.00 | 0.00 | 0.00 | 0.00 | 0.00 | 0.00 |
| Total H2, MMSCFD | 5.84 | 4.25 | 2.14 | 1.16 | 0.54 | 0.25 | 0.09 | 0.00 | 0.00 |
| Syngas H2:CO Ratio (pre membrane) | 3.29 | 2.95 | 2.53 | 2.34 | 2.23 | 2.17 | 2.14 | 2.10 | 2.05 |
| Stream 315 H2:CO Ratio (Syngas to FT) | 2.13 | 2.13 | 2.13 | 2.13 | 2.13 | 2.13 | 2.13 | 2.10 | 2.05 |
| Power Generated, kW | 513 | 501 | 492 | 490 | 488 | 488 | 487 | 485 | 480 |
| Power Required, kW | 513 | 501 | 492 | 490 | 488 | 488 | 487 | 485 | 480 |

Steam to carbon ratio: 2.0; OTM outlet pressure: 460 psia; OTM outlet temperature: 1800 F.; FT product rate: 400 BBL/d

TABLE 4

| FT Tail Gas to Syngas Process | 0% | 30% | 60% | 70% | 75% | 77% | 78% | 79% | 80% |
|---|---|---|---|---|---|---|---|---|---|
| Stream 315 (Syngas to FT) Composition (%) | | | | | | | | | |
| Hydrogen | 58.474 | 57.723 | 56.342 | 55.512 | 54.923 | 54.623 | 54.455 | 53.988 | 53.133 |
| Nitrogen | 0.383 | 0.467 | 0.658 | 0.794 | 0.896 | 0.948 | 0.977 | 1.016 | 1.070 |
| Water | 0.258 | 0.282 | 0.319 | 0.338 | 0.351 | 0.358 | 0.361 | 0.364 | 0.365 |
| Carbon monoxide | 27.491 | 27.138 | 26.489 | 26.099 | 25.822 | 25.681 | 25.602 | 25.660 | 25.894 |
| Carbon dioxide | 12.299 | 13.483 | 15.516 | 16.682 | 17.494 | 17.904 | 18.133 | 18.517 | 19.107 |
| Methane | 1.093 | 0.905 | 0.674 | 0.574 | 0.511 | 0.485 | 0.471 | 0.453 | 0.430 |
| Ammonia | 0.002 | 0.002 | 0.002 | 0.002 | 0.002 | 0.002 | 0.002 | 0.002 | 0.002 |

Steam to carbon ratio: 2.0; OTM outlet pressure: 460 psia; OTM outlet temperature: 1800 F.; FT product rate: 400 BBL/d

The invention claimed is:

1. A method for producing a synthesis gas in an oxygen transport membrane based reforming system configured for use in a Fischer-Tropsch process, the method comprising the steps of:

reforming a feed stream in a reforming reactor in the presence of steam, heat and a reforming catalyst disposed in the reforming reactor to produce a reformed synthesis gas stream comprising hydrogen, carbon monoxide, and unreformed hydrocarbon gas;

further reforming the reformed synthesis gas stream in the presence of one or more catalysts contained in an oxygen transport membrane based reforming reactor, reaction products and heat to produce a synthesis gas product stream;

wherein a portion of the heat required for the reforming of the feed stream is transferred via radiation from the oxygen transport membrane based reforming reactor which is disposed proximate the reforming reactor; and wherein the feed stream comprises a methane containing feed and a tail gas feed wherein the tail gas feed is produced in the Fischer-Tropsch process.

2. The method of claim 1 wherein the step of further reforming the reformed synthesis gas stream in the presence of one or more catalysts contained in the oxygen transport membrane based reforming reactor, reaction products and heat further comprises:

feeding the reformed synthesis gas stream to a reactant side of a reactively driven and catalyst containing oxygen transport membrane based reforming reactor, wherein the oxygen transport membrane based reforming reactor includes at least one oxygen transport membrane element configured to separate oxygen from an oxygen containing stream at an oxidant side of the reactively driven and catalyst containing oxygen transport membrane reforming reactor to the reactant side through oxygen ion transport when subjected to an elevated operational temperature and a difference in oxygen partial pressure across the at least one oxygen transport membrane element;

reacting a portion of the reformed synthesis gas stream at the reactant side of the reactively driven and catalyst containing oxygen transport membrane based reforming reactor with oxygen permeated through the at least one oxygen transport membrane element to produce the difference in oxygen partial pressure across the at least one oxygen transport membrane element, reaction products, heat, including the radiant heat transferred to the reforming reactor for the reforming of the feed stream; and reforming the unreformed hydrocarbon gas in the reformed synthesis gas stream in the oxygen transport membrane based reforming reactor in the presence of the catalysts, the reaction products and the heat to produce the synthesis gas product stream.

3. The method of claim 1 wherein the ratio of H2/CO in the synthesis gas product stream is about 1.7 to about 2.9.

4. The method of claim 3 wherein the ratio of H2/CO in the synthesis gas product stream is about 1.9 to about 2.2.

5. The method of claim 1 wherein the feed stream comprises from about 20% to about 45% by volume of the tail gas feed.

6. The method of claim 1 wherein from about 50% to about 80% by volume of the tail gas produced in the Fischer-Tropsch process is diverted to the feed stream.

7. The method of claim 1 wherein the feed stream comprises from about 55% to about 80% by volume of the methane containing feed.

8. The method of claim 1 further comprising the steps of diverting a portion of the synthesis gas product stream to a hydrogen separation membrane to produce a hydrogen rich stream and a carbon monoxide rich stream.

9. The method of claim 8 further comprising the step of sending the hydrogen rich stream to a pressure swing adsorption unit to generate a high purity hydrogen stream and a hydrogen containing tail gas.

10. The method of claim 1 further comprising the steps of diverting a portion of the synthesis gas product stream to a hydrogen separation membrane to produce a hydrogen rich stream and a carbon monoxide rich stream wherein the carbon monoxide rich stream is recombined with the synthesis gas product stream to produce a conditioned synthesis gas stream wherein the conditioned synthesis gas stream has a H2/CO ratio of about 1.7 to about 2.2.

11. The method of claim 10 wherein less than about 25% of the synthesis gas product stream is diverted to the hydrogen separation membrane.

12. A method for producing a liquid hydrocarbon product from a Fischer-Tropsch process, the method comprising the steps of:
    reforming a feed stream in a reforming reactor in the presence of steam, heat and a reforming catalyst disposed in the reforming reactor to produce a reformed synthesis gas stream comprising hydrogen, carbon monoxide, and unreformed hydrocarbon gas;
    further reforming the reformed synthesis gas stream in the presence of one or more catalysts contained in an oxygen transport membrane based reforming reactor, reaction products and heat to produce a synthesis gas product stream;
    synthesizing the synthesis gas product stream using a Fischer-Tropsch process to produce the liquid hydrocarbon product and a Fischer-Tropsch tail gas;
    wherein a portion of the heat required for the reforming of the feed stream is transferred via radiation from the oxygen transport membrane based reforming reactor which is disposed proximate the reforming reactor; and
    wherein the feed stream comprises a methane containing feed and a portion of the Fischer-Tropsch tail gas.

13. The method of claim 12 wherein the ratio of H2/CO in the synthesis gas product stream is about 1.7 to about 2.9.

14. The method of claim 12 wherein the portion of the Fischer-Tropsch tail gas that comprises the feed stream is from about 50% to about 80% by volume of the Fischer-Tropsch tail gas.

15. The method of claim 12 wherein the feed stream comprises from about 20% to about 45% by volume of the Fischer-Tropsch tail gas feed.

16. The method of claim 12 wherein the feed stream comprises from about 55% to about 80% by volume of the methane containing feed.

17. The method of claim 12 wherein the step of further reforming the reformed synthesis gas stream in the presence of one or more catalysts contained in the oxygen transport membrane based reforming reactor, reaction products and heat further comprises:
    feeding the reformed synthesis gas stream to a reactant side of a reactively driven and catalyst containing oxygen transport membrane based reforming reactor, wherein the oxygen transport membrane based reforming reactor includes at least one oxygen transport membrane element configured to separate oxygen from an oxygen containing stream at an oxidant side of the reactively driven and catalyst containing oxygen transport membrane reforming reactor to the reactant side through oxygen ion transport when subjected to an elevated operational temperature and a difference in oxygen partial pressure across the at least one oxygen transport membrane element;
    reacting a portion of the reformed synthesis gas stream at the reactant side of the reactively driven and catalyst containing oxygen transport membrane based reforming reactor with oxygen permeated through the at least one oxygen transport membrane element to produce the difference in oxygen partial pressure across the at least one oxygen transport membrane element, reactions products, and heat, including the radiant heat transferred to the reforming reactor for the reforming of the feed stream; and
    reforming the unreformed hydrocarbon gas in the reformed synthesis gas stream in the oxygen transport membrane based reforming reactor in the presence of the catalysts, the reaction products and the heat to produce the synthesis gas product stream.

18. The method of claim 12 further comprising the steps of diverting a portion of the synthesis gas product stream to a hydrogen separation membrane to produce a hydrogen-rich stream and a carbon monoxide rich stream wherein the carbon monoxide rich stream is recombined with the synthesis gas product stream to produce a conditioned synthesis gas stream wherein the conditioned synthesis gas stream has a H2/CO ratio of about 1.7 to about 2.2.

19. The method of claim 18 wherein less than about 25% of the synthesis gas product stream is diverted to the hydrogen separation membrane.

20. The method of claim 18 further comprising the step of sending the hydrogen rich stream to a pressure swing adsorption unit to generate a high purity hydrogen stream and a hydrogen containing tail gas.

21. The method of claim 12 wherein the Fischer-Tropsch process comprises a Fischer-Tropsch reactor selected from the group consisting essentially of a fixed bed reactor, a slurry phase reactor, a synthol reactor, or a microchannel reactor.

22. The method of claim 18 wherein the Fischer-Tropsch process is a multi-stage Fischer-Tropsch process comprising two or more Fischer-Tropsch reactors and a portion of the hydrogen-rich stream is fed to one or more of the Fischer-Tropsch reactors.

* * * * *